(12) United States Patent
Jennings et al.

(10) Patent No.: US 12,290,109 B2
(45) Date of Patent: May 6, 2025

(54) VAPOR SAMPLE COLLECTION APPARATUS AND METHOD FOR VAPOR SAMPLE COLLECTION

(71) Applicant: The Green Labs Group Inc., Los Angeles, CA (US)

(72) Inventors: Aric Jennings, Los Angeles, CA (US); Steven L Hecker, Los Angeles, CA (US); Kyle Patrick Crane Rodrigues, Los Angeles, CA (US)

(73) Assignee: The Green Labs Group, Inc., Los Angeles, CA (US)

( * ) Notice: Subject to any disclaimer, the term of this patent is extended or adjusted under 35 U.S.C. 154(b) by 644 days.

(21) Appl. No.: 17/351,158

(22) Filed: Jun. 17, 2021

(65) Prior Publication Data

US 2021/0310909 A1    Oct. 7, 2021

Related U.S. Application Data

(63) Continuation-in-part of application No. PCT/US2021/022787, filed on Mar. 17, 2021.

(Continued)

(51) Int. Cl.
*A24F 40/53* (2020.01)
*A24F 40/65* (2020.01)
(Continued)

(52) U.S. Cl.
CPC .............. *A24F 40/53* (2020.01); *A24F 40/65* (2020.01); *A61M 11/041* (2013.01);
(Continued)

(58) Field of Classification Search
CPC ....... A24F 40/53; A24F 40/65; A61M 11/041; A61M 11/042; A61M 15/0021;
(Continued)

(56) References Cited

U.S. PATENT DOCUMENTS

| 11,633,554 B1 | 4/2023 | Puviani et al. |
| 2009/0293892 A1 | 12/2009 | Williams et al. |

(Continued)

FOREIGN PATENT DOCUMENTS

| CN | 204273249 U | 4/2015 |
| CN | 105411004 A | 3/2016 |

(Continued)

OTHER PUBLICATIONS

CN-201780075323.9 Chinese First Office Action of Chinese Patent Office dated Jan. 18, 2021.

(Continued)

*Primary Examiner* — Jonathan M Dunlap
*Assistant Examiner* — John M Royston
(74) *Attorney, Agent, or Firm* — Ashfields Law P. C.

(57) ABSTRACT

A vapor sample collection apparatus and method of vapor sample collection. The vapor sample collection apparatus has a connection port to connect a first end of a tube to an exhaust port of a vaporizer device, a vacuum pump connected to a second end of the tube, a manifold connected to the vacuum pump, and a vapor containment vessel for collecting a vapor sample, where the vacuum pump is configured to draw a predetermined pressure on the tube. The method of vapor sample collection includes connecting a connection port to an exhaust port of a vaporizer device, the connection port being attached to a first end of a tube, activating the vaporizer device to vaporize a sample containing an active ingredient, drawing a predetermined pressure on a second end of the tube using a vacuum pump, and collecting a vapor sample from the vaporizer device in a vapor containment vessel.

21 Claims, 11 Drawing Sheets

Related U.S. Application Data

(60) Provisional application No. 62/993,211, filed on Mar. 23, 2020, provisional application No. 62/990,769, filed on Mar. 17, 2020.

(51) Int. Cl.
| | |
|---|---|
| *A61M 11/04* | (2006.01) |
| *A61M 15/00* | (2006.01) |
| *A61M 15/06* | (2006.01) |
| *G01N 1/24* | (2006.01) |
| *G01N 30/02* | (2006.01) |
| *G01N 30/22* | (2006.01) |
| *G01N 33/00* | (2006.01) |
| *G06F 16/22* | (2019.01) |
| *G06F 16/2455* | (2019.01) |
| *G06F 16/9535* | (2019.01) |
| *G06N 20/00* | (2019.01) |
| *H01J 49/04* | (2006.01) |
| *H04L 67/10* | (2022.01) |

(52) U.S. Cl.
CPC ...... *A61M 11/042* (2014.02); *A61M 15/0021* (2014.02); *A61M 15/0065* (2013.01); *A61M 15/06* (2013.01); *G01N 1/24* (2013.01); *G01N 30/22* (2013.01); *G01N 33/0062* (2013.01); *G06F 16/22* (2019.01); *G06F 16/2455* (2019.01); *G06F 16/9535* (2019.01); *G06N 20/00* (2019.01); *H01J 49/0422* (2013.01); *A61M 2205/3334* (2013.01); *A61M 2205/3368* (2013.01); *A61M 2205/3553* (2013.01); *A61M 2205/502* (2013.01); *G01N 2030/027* (2013.01); *G01N 33/0068* (2024.05); *H04L 67/10* (2013.01)

(58) Field of Classification Search
CPC .............. A61M 15/0065; A61M 15/06; A61M 2205/3334; A61M 2205/3368; A61M 2205/3553; A61M 2205/502; G01N 1/24; G01N 30/22; G01N 33/0062; G01N 2030/027; G01N 2033/0068; G06F 16/22; G06F 16/2455; G06F 16/9535; G06N 20/00; H04L 67/10; H01J 49/0422
See application file for complete search history.

(56) References Cited

U.S. PATENT DOCUMENTS

| | | | |
|---|---|---|---|
| 2013/0247910 | A1 | 9/2013 | Postma |
| 2014/0174383 | A1 | 6/2014 | Kesten et al. |
| 2016/0211693 | A1 | 7/2016 | Stevens et al. |
| 2016/0235124 | A1 | 8/2016 | Krietzman |
| 2016/0331027 | A1* | 11/2016 | Cameron ............... B05B 15/40 |
| 2016/0370337 | A1 | 12/2016 | Blackley |
| 2017/0304563 | A1 | 10/2017 | Adelson |
| 2018/0093054 | A1 | 4/2018 | Bowen et al. |
| 2019/0240430 | A1 | 8/2019 | Jackson et al. |
| 2019/0387796 | A1* | 12/2019 | Cohen .................... A24F 40/30 |
| 2020/0085109 | A1* | 3/2020 | Manca ................... A24F 40/60 |

FOREIGN PATENT DOCUMENTS

| | | |
|---|---|---|
| EP | 3205220 A1 | 8/2017 |
| WO | 2006082571 A1 | 8/2006 |
| WO | 2012040512 A2 | 3/2012 |
| WO | 2013102609 A2 | 7/2013 |
| WO | 2019204812 A1 | 10/2019 |

OTHER PUBLICATIONS

EP-17784383.6 European first office action dated Feb. 10, 2021.
PCT/GB2017/053049 International search report and written opinion of international searching authority mailed Jan. 17, 2018.
PCT/US2021/022787 Invitation to Pay Additional Fees of the international searching authority mailed Jun. 2, 2021.
International search report and written opinion of international searching authority for PCT application PCT/US2021/022787 mailed Jul. 21, 2021.

\* cited by examiner

VAPOR SAMPLE COLLECTION APPARATUS AND METHOD FOR VAPOR SAMPLE COLLECTION

CROSS-REFERENCE TO RELATED APPLICATIONS

This application claims priority to: PCT Patent Application No. PCT/US2021/022787, entitled "Accurate Dosing of Vaporizer Content," filed Mar. 17, 2021, which claims priority to U.S. Provisional Patent Application No. 62/990,769, entitled "System for the capturing and quantification of vapor content," filed Mar. 17, 2020, and also claims priority to U.S. Provisional Patent Application No. 62/993,211, entitled "System for the use of polynomial driven vapor dosage calculations," filed Mar. 23, 2020, all of which are herein incorporated by reference in their entirety.

FIELD OF INVENTION

The present disclosure generally relates to controlling doses of active ingredients from vaporizers, and more specifically relates to quantifying the dose of active ingredients in relation to vaporizer operating parameters.

BACKGROUND

A vaporizer is a device used to extract the active ingredients of a material, typically plant material such as herbs or herbal blends, for inhalation by a user. Vaporization involves heating the material to extract its active compounds as a vapor. In contrast, smoking involves the release of active compounds through combustion, typically with other particulate matter, noxious gasses, and possible carcinogens. Interest in vaporizers for both recreational and medical use has increased recently, in part from the reduced risks compared to smoking.

In comparison to other drug delivery methods, such as ingestion, vaporization has a more rapid onset of pharmacological effect, direct delivery into the bloodstream via the lungs, and more precise titration such that the desired level is reached and not exceeded, enabling consistent and appropriate dosage.

Vaporizers utilizing convection-based heating methods employ the use of a heating element. Air is drawn into the vaporizer, heated by the heating element, and then passes across the material to extract its active ingredients as a vapor. The heated air and vaporized active ingredients are then delivered to the user via a mouthpiece. The air temperature needed to extract active ingredients from an herbal material varies depending on the herbal material, but generally ranges from 180 to 360° C.

When a user inhales too much vapor from the vaporizer device, the user may experience an undesirable amount of the effects of the active ingredients.

BRIEF SUMMARY

Controlling the amount of active ingredient(s) or dose in vapor being drawn, or informing the user as to the amount of vapor and active ingredient(s) being drawn, or available to be drawn can allow the user to better control the resulting effects. Thus, it is preferable to provide a vaporizer device that is capable of monitoring and/or controlling the mass flow rate within the vaporizer device to regulate the dosage of active ingredients being inhaled by the user. Correlating the vaporizer device parameters with a particular sample, and providing a desired dose based on a predicted dosing calculation allows the device to deliver specified quantity or dose of active ingredients.

The embodiments of the present disclosure provide devices, vapor management systems and methods that can capture, quantify, analyze, and correlate data from vaporizer devices and the vaporized product, and provide suggested vaping profiles to vaporizer devices for desired dosing.

In one aspect of the disclosure, a vaporizer device includes a receptacle for holding material having an active ingredient, a heating element for heating the receptacle or for heating air as it flows to the receptacle, a controller configured to receive vapor production information from sensors inside the vaporizer device. The controller is also configured to generate vapor production data including a sample identifier associated with the material and at least one of the following: crucible temperature, vapor temperature, vapor flow rate, vapor pressure, vapor flow duration, vapor density, heating duration, material pack density, and heating power. The vaporizer device also includes an electronic memory configured to store the vapor production data. In some embodiments, various sensors may be used, such as, a crucible temperature sensor, a vapor temperature sensor, a vapor flow rate sensor, a vapor pressure sensor, a vapor flow duration sensor, a pressure differential sensor, and a vapor density sensor.

According to another aspect of the disclosure, a method of using a vaporizer device includes providing material having an active ingredient and heating the receptacle or heating air as it flows to a receptacle containing the material. Vapor production information is received from sensors inside the vaporizer device, and vapor production data is generated that includes a sample identifier associated with the material and at least one parameter, selected from the following: crucible temperature, vapor temperature, vapor flow rate, vapor pressure, vapor flow duration, vapor density, heating duration, material pack density, pressure differential, material age, and heating power. The method also stores the vapor production data. In an embodiment, vapor production data over a communications network to a vapor profile management system.

According to another embodiment of the disclosure, a vaporizer profile management system (VPMS) includes a vaporizer device that has an electronic memory configured to store vapor production data for a sample material having an active ingredient. The vapor production data includes a sample identifier, and data concerning at least one of the following: an active ingredient, crucible temperature, air flow rate, and duration of flow. The vaporizer device also has a communications interface configured to transmit the stored vapor production data to a computing platform. The VPMS also includes a vapor analyzing device that is configured to generate vapor content data derived from vapor collected from an exhaust port of the vaporizer device. The vapor content data includes the sample identifier and data including concentration of the active ingredient. The VPMS also includes a computing platform configured to receive and process the vapor production data and the vapor content data.

Yet another embodiment of the disclosure includes providing a vapor data repository. This may include electronic storage for vapor production data from a vaporizer device, in which the vapor production data includes a sample identifier associated with material having an active ingredient and vaping parameters. The vaping parameters may include at least one of the following: crucible temperature, vapor temperature, vapor flow rate, vapor pressure, vapor flow duration, vapor density, heating duration, vapor pressure differential, material age, and heating power. The vapor data repository may also have electronic storage for vapor content data that includes concentration of active ingredient data captured by a vapor sample collection apparatus.

In still another embodiment, a vapor sample collection apparatus may include a connection port adapted to connect a first end of a tube to an exhaust port of a vaporizer device, a vacuum pump connected to a second end of the tube, a manifold connected to the vacuum pump, and a vapor containment vessel for collecting vapor samples. The vacuum pump is configured to draw a predetermined pressure on the tube.

In still another embodiment, a vaporizer device has a receptacle for holding material having an active ingredient. The vaporizer device also has a heating element for heating air as it flows to the receptacle, as well as an electronic storage memory for storing vapor correlation data. The device also has a controller configured to control at least one vaporizer parameter according to instructions in the vapor correlation data and a requested dose of active ingredient, such that at least one vaporizer parameter includes at least one of temperature, air flow rate, and duration per use.

DETAILED DESCRIPTION

Example embodiments will now be described hereinafter with reference to the accompanying drawings, which form a part hereof, and which illustrate example embodiments which may be practiced. As used in the disclosures and the appended claims, the terms "embodiment", "example embodiment", and "exemplary embodiment" do not necessarily refer to a single embodiment, although they may, and various example embodiments may be readily combined and interchanged, without departing from the scope or spirit of example embodiments.

Furthermore, the terminology as used herein is for the purpose of describing example embodiments only and is not intended to be limitations. In this respect, as used herein, the term "in" may include "in" and "on", and the terms "a," "an" and "the" may include singular and plural references. Furthermore, as used herein, the term "by" may also mean "from", depending on the context. Furthermore, as used herein, the term "if" may also mean "when" or "upon," depending on the context. Furthermore, as used herein, the words "and/or" may refer to and encompass any and all possible combinations of one or more of the associated listed items. It will be appreciated by those of ordinary skill in the art that the embodiments disclosed herein can be embodied in other specific forms without departing from the spirit or essential character thereof. The presently disclosed embodiments are therefore considered in all respects to be illustrative and not restrictive.

Figure 1A:
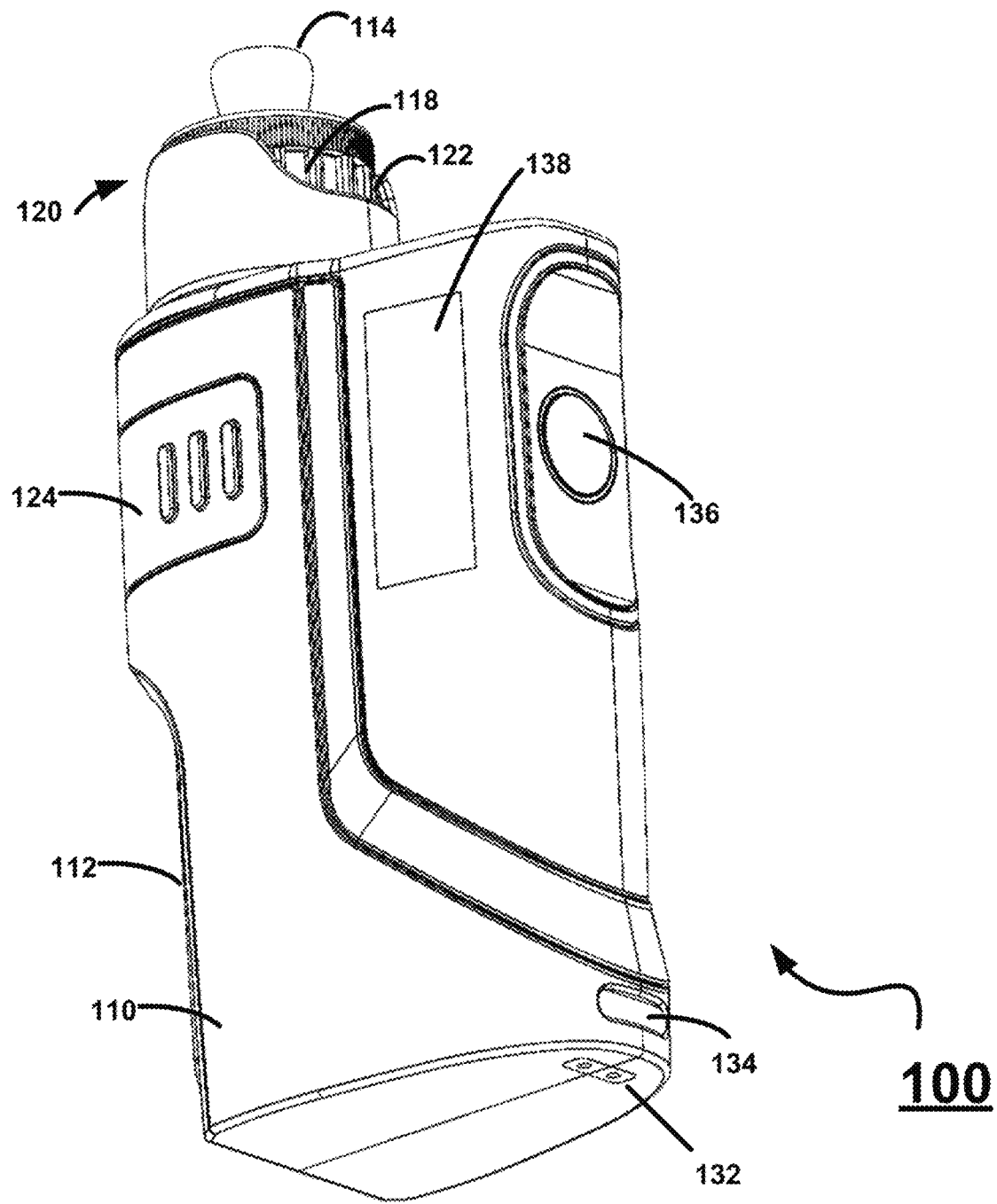
FIG. 1A is a diagram of an embodiment of a vaporizer in accordance with the present disclosure.
Figure 1B:
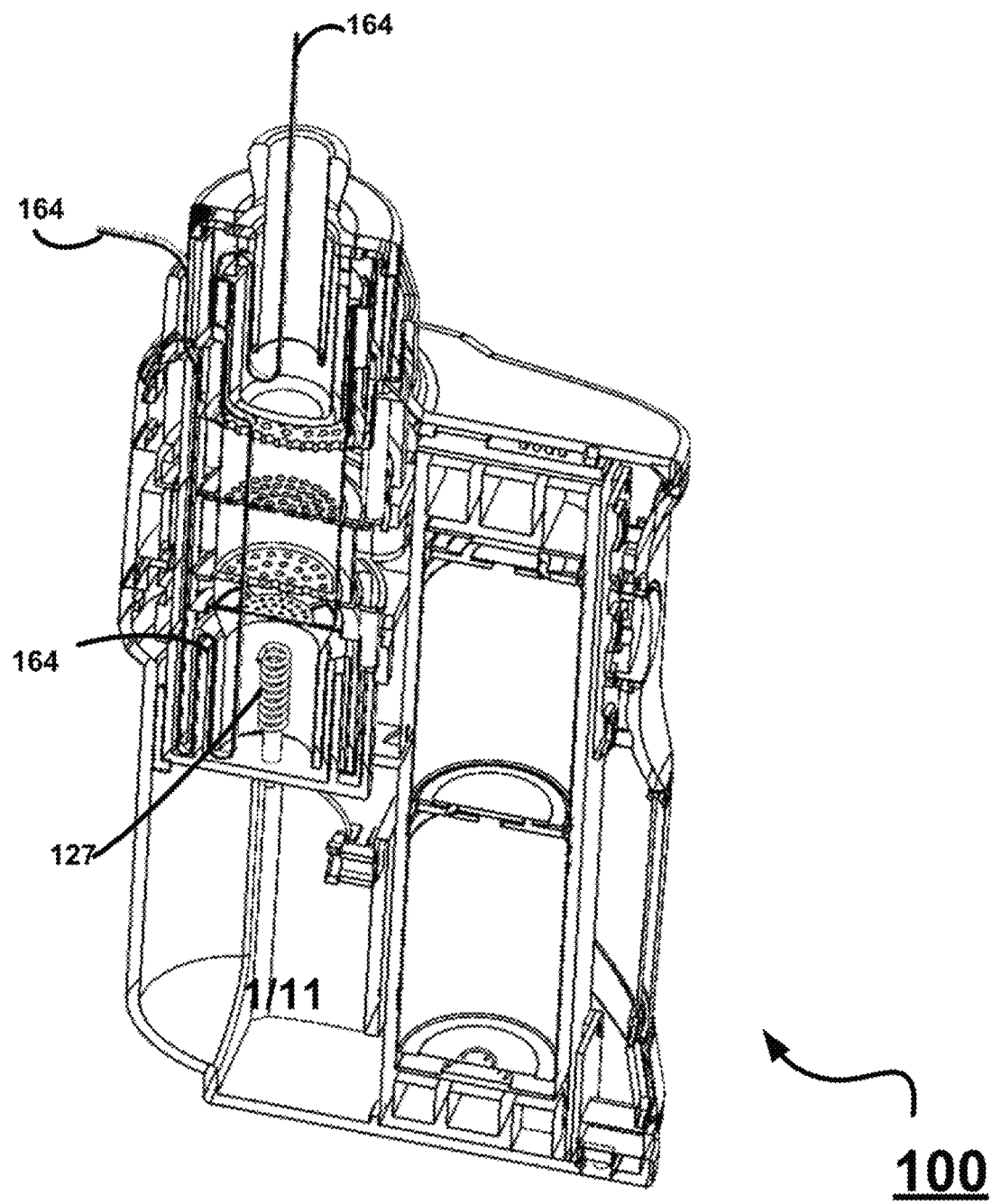
FIG. 1B is a sectioned diagram of an embodiment of a vaporizer in accordance with the present disclosure.
Figure 1C:
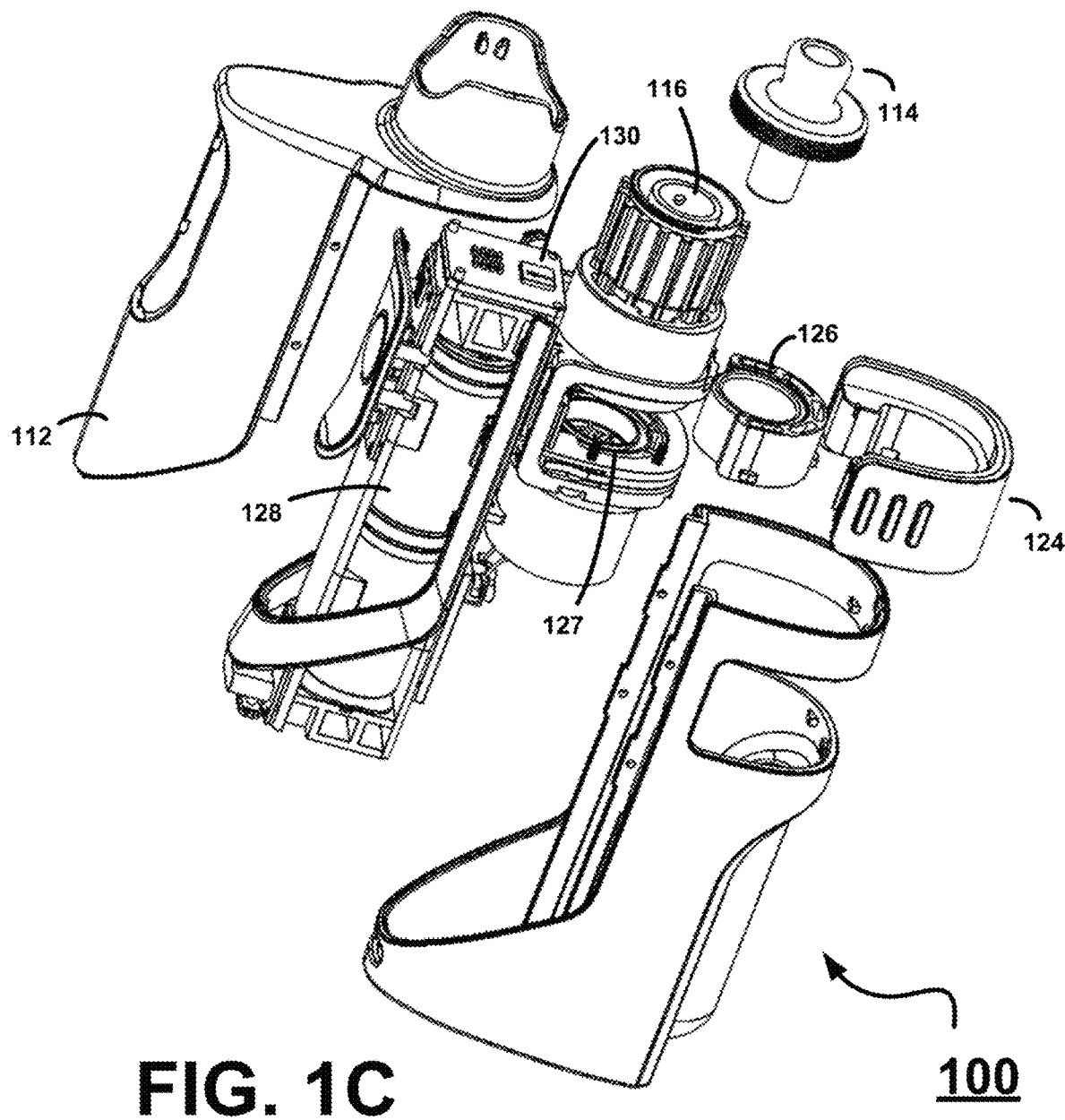
FIG. 1C is an exploded diagram of an embodiment of a vaporizer in accordance with the present disclosure.

FIG. 1A is a perspective diagram, FIG. 1B is a cross-sectional diagram, and FIG. 1C is an exploded perspective diagram of an embodiment of a vaporizer device 100.

Vaporizer device 100 has a body 110 with an outer case 112. The body 110 is of a size and shape to allow the vaporizer device 100 to be comfortably held in a user's hand. A mouthpiece 114 is provided at an exhaust port 116 at one end of the body 112, from which heated air and active ingredient(s) exit the vaporizer device 100. A user may inhale on the mouthpiece 114 to receive the heated air and active ingredients. The outer case 112 has an opening 118 proximate to the exhaust port 116. The opening 118 defines an inlet 120 to the vaporizer device 100. Air is drawn into the vaporizer device 100 at the inlet 120 as the user inhales on the mouthpiece 114.

Depending on the material containing active ingredient(s) used with the vaporizer device 100, the temperature of the heated air or the temperature of the crucible required to extract the material's active ingredients may be too high for a user to comfortably inhale. In some embodiments, the active material may be in a liquid or a wax form and put in a crucible that is heated to release the active material as vapor. In other embodiments, the active material may be in a solid, semi-solid, crystalline, crushed, shredded, or powder form (or the like) in which it is placed in a crucible that receives heated air over or through it in order to release the active ingredient as vapor. The vaporizer device 10 may include a heatsink 122 that absorbs heat from the heated air and active ingredient(s) prior to entering the mouthpiece 114, cooling the air and active ingredient(s) inhaled by the user. The inlet 120 is provided adjacent the heatsink 122. Locating the inlet 120 near the heatsink 122 allows air being drawn into the inlet 120 to be warmed by the heatsink 122.

The vaporizer device 100 includes a receptacle 126 into which material containing active ingredient(s) may be placed by the user. A door 124 may be hinged to the body 110 to provide the user with access to the receptacle 126 in order to add material to or remove spent material from the receptacle 126.

In use, in an embodiment, air flows into the vaporizer device 100, to a heating device 127 where it is heated, across the material in the receptacle 126 where active ingredient(s) are extracted by the heat into the air and delivered to the user. As mentioned above, in another embodiment, the crucible may be heated directly to release the active ingredient as vapor. In each embodiment, it should be apparent to the person of ordinary skill that heat transfer by conductive, convective, or radiative techniques may be used to extract the active ingredient as vapor. The temperature can be adjustable by the user via controls on the device or via a vaporizer application 182 or app on a communicatively coupled handheld electronic device 180. The path of the airflow from inlet 120 to exhaust at mouthpiece 114 is shown by flow pathway 164.

The vaporizer device 100 can include a power source, for example a battery 128. As used here, the term battery means a single battery or several batteries connected to provide a portable power source, preferably integrated within the body 110 of vaporizer device 100, although in some embodiments, an external battery or power source may be connected to provide primary or supplementary power to vaporizer device 100. Any desired type of battery 128 can be used depending on design parameters such as power requirements and size and weight restrictions. Batteries can be removable or fixed and can be rechargeable or non-rechargeable. With use of a rechargeable battery, charge circuitry and power management circuitry may be utilized in the vaporizer device 100 to optimize recharging, charge storage, discharge management, and provide charge status to display 138 or application 182. Battery 128 may be charged via a power cord physically connected to vaporizer device 100, via physical electrical contacts on a charge port 132 with a charge cradle connected to a power supply (not shown), via a communications port 134 (e.g., a USB port), or via wireless inductive charge techniques, for example, Qi, which is an open interface standard that defines wireless power transfer using inductive charging.

The vaporizer device 100 can further include controller 130 for allowing the user to control parameters of the vaporizer device, for example the temperature, air flow rate, and/or duration per use. For example, duration can be controlled by the controller 130 by controlling the delivery of power and heating time of the heating element. The controller 130 can be analogue or digital discrete circuitry and can include a central processing unit ("CPU"), microprocessor, system on a chip ("SOC"), an application specific integrated circuit ("ASIC"), an embedded controller, Field Programmable Gate Array ("FPGA"), or other appropriate controller devices, and any combination thereof.

The controller 130 can also include memory 133 or other data storage 135. The controller 130 can store vapor production data 190 as well as vaporizer profiles associated with a medium described herein as vapor correlation data 550. Creation and use of such vaporizer profiles/vapor correlation data 550 is discussed in more detail in the foregoing specification. The controller 130 can also store historic data, such as duration of use, temperature profile, and vapor mass flow, among others. The controller 130 can also store a unique identifier for the vaporizer device 100 that allows it to be identified and associated with a user when the VPMS 300 remotely connects to or receives data from it.

The vaporizer profiles may be programmed manually or provided via communications network 170, and the controller 130 may include communications interface circuitry 140. In an embodiment, the mobile device 180 may receive the vaporizer profile from VPMS 300 via the network 170 and in turn provide it to the controller 130 of the vaporizing device 100 in real time, on demand, or during periodic data downloads. The network 170 may include different channels of communication and may include local networks therein. For example, the network 170 may include wireless communication through cellular networks, Wi-Fi, Bluetooth, Zigbee, or any combination thereof, as well as physical connections via a cable, for example, a Universal Serial Bus ("USB") port 134 or the like. Additionally, the vaporizer device 100 may be connected to communications network 170 via a wired or wireless local communication connection through mobile device 180 that may have a vaporizer application 182 installed thereon. The network 170 may include one or more switches and/or routers, including wireless routers that connect the wireless communication channels with other wired networks (e.g., the Internet). A local network may exist that connects locally to the VPMS 300 or the vaporizer device 100. For example, the local network may be established by a local router or a local switch.

In some embodiments, the VPMS 300 can communicate with a mobile device 180, for example a smartphone, tablet, or Internet of Things (IoT) device. In such embodiments, VPMS 300 may communicate with a solution-specific application 182 installed on the mobile device 180. The application can include a user interface to allow a user to read, interact, and respond to information from the VPMS 300. The VPMS 300 can be configured to communicate to the mobile device 180 any of the information discussed herein as being communicated with the vaporizer device 100. In some embodiments, the mobile device 180 can be configured to communicate any, or none, of the information with the vaporizer device 100.

Some embodiments of vaporizer device 100 can include user input controls 136, such as buttons or switches. The vaporizer device 100 can provide feedback to the user by means of a display 138. Some display embodiments can include a plurality of light-emitting diodes (LEDs). The LEDs may be activated individually or together, may be configured to flash at one or more speeds or may be on continuously, and may each be a single color or multi-color, or combinations of these to provide a range of indications to the user. Such indications may include charge status of the battery, an 'on' state of the device 100, and whether the vaporizer device 100 is ready for use. Display 138 may also be an LCD, or OLED display, or other known addressable display technology for interfacing with and presenting information to a user. Display 138 may also have a touch-sensitive user interface instead of or in addition to user input controls 136 for the purpose of operating and interacting with vaporizer device 100.

Controller 130 may receive sensor information from different sensors 150 within the vaporizer device 100. For example, the controller 130 may collect data from a thermocouple(s) 152 that may measure crucible temperature, air flow rate sensor(s) 154, pressure sensor(s) 156, vapor density sensor(s) 158, mass flow rate analyzer(s) 160. It is to be understood that the individual measuring or sensor devices within the vaporizer device 100 are in electrical communication with the controller 130.

A mass flow rate analyzer 160 may be a miniature mass spectrometer for in situ analysis, a photodiode with a phototransistor array, a particle counter or smoke detector, or any other suitable device for measuring mass flow rate within the vaporizer device 100. In an embodiment, at least one photodiode with a phototransistor array is disposed within a sensor ring. The sensor ring of photodiodes may circumscribe a mouthpiece of the vaporizer device with a phototransistor array including a set of emitting diodes disposed on opposite sides of the mouthpiece. Alternatively, the sensor ring may be disposed within a cavity formed below the mouthpiece. In one embodiment, the sensor ring may be disposed above the crucible. The attenuation of light signal from photodiode to phototransistor sensor may provide optical transmission data that can indicate vapor density. Using photodiodes of different wavelengths and/or wavelength tunable photodiodes in the phototransistor array many provide various data related to particulates in the vapor.

Air flow rate sensor 154 may be provided in the air passageway within vaporizer device 100 and may provide the rate of flow. An exemplary flow rate sensor 154 may be provided by an impellor-driven generator, or a solid-state sensor that can measure flow rate.

A pair of pressure sensors 156 may be used to measure flow rate, each pressure sensor being located at different places in the air passageway, for example in an embodiment, a first sensor located after the crucible and another downstream before the mouthpiece. The differential in pressure may be used to calculate a flow rate.

Vapor density within the vaporizer device 100 may also be calculated based on the volume of the air passageway and the mass of the vapor.

Another input that may be received by the controller 130 is the age of the material, since the material may have a shelf life that is directly related to the yield of the material when vaporized.

Yet another input that may be received by the controller 130 is previous vaporizing history of the material, in that it may have been used in previous vaporizing sessions, and the sensors have recorded parameters regarding those sessions. These recorded parameters may be used to calculate used active ingredient for a dosage history and/or provide remaining active ingredient, remaining potency, or remaining dose information for subsequent vaporizer activations.

In some embodiments, the vaporizing medium can be detected by the vaporizing device 100 by use of an optical sensor on the vaporizer device itself or the connected application 182 on mobile device 180, for scanning barcodes on capsules or packages of the herbal medium that identify the contents. As will be appreciated by a person of ordinary skill, there are many ways of calculating flow rate, temperature, vapor density, and so on. The present teachings give some examples of data that may be collected and used to determine such variables.

Figure 2:
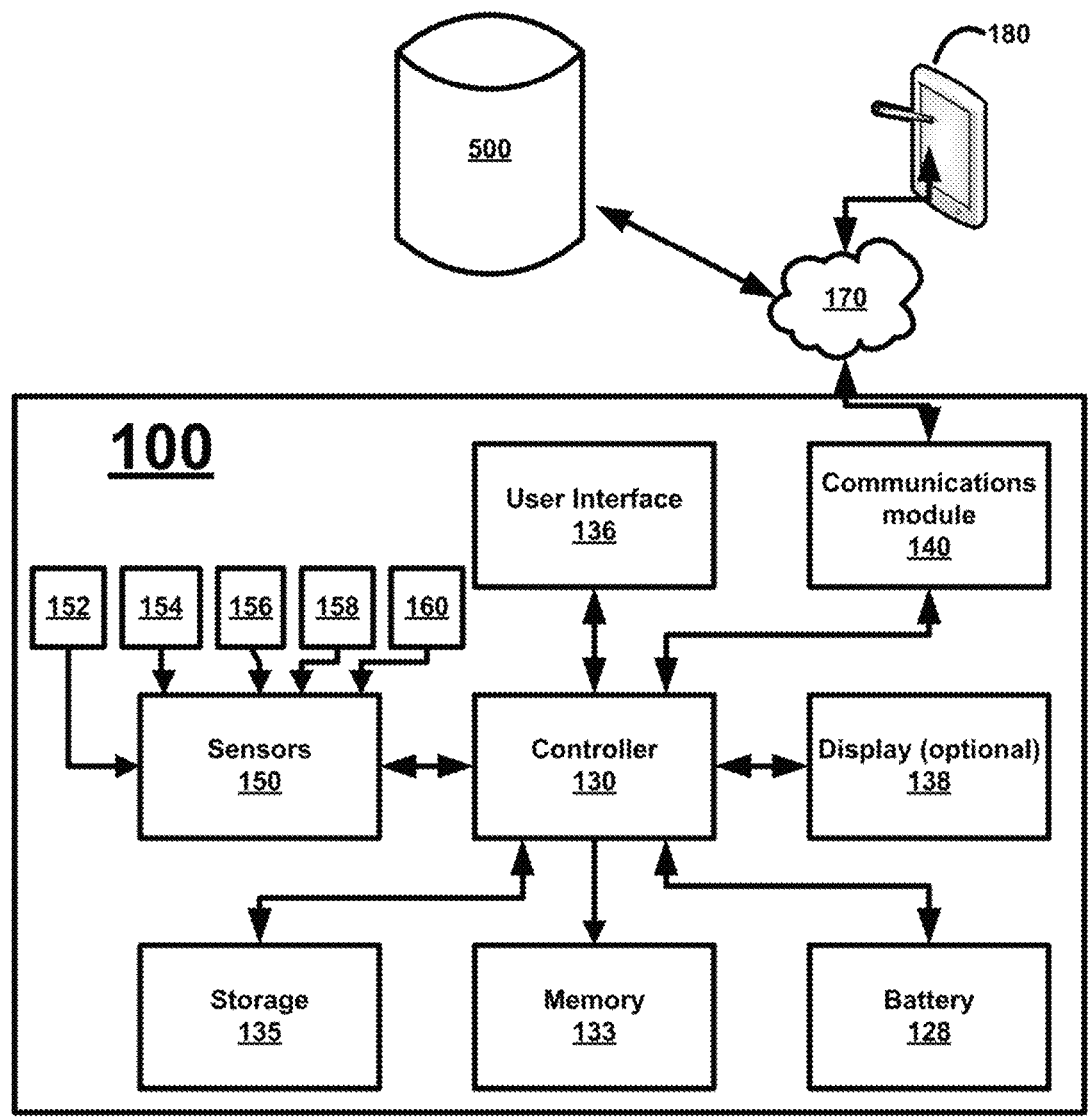
FIG. 2 is a schematic diagram of an embodiment of a vaporizer device in accordance with the present disclosure.

FIG. 2 is a schematic diagram of a vaporizer device in accordance with the present disclosure. As described in FIG. 1, the various components are communicatively coupled or electrically coupled as shown in the figure. As may be appreciated by a skilled artisan, there may be interface devices between the various schematic functional blocks.

Figure 3:
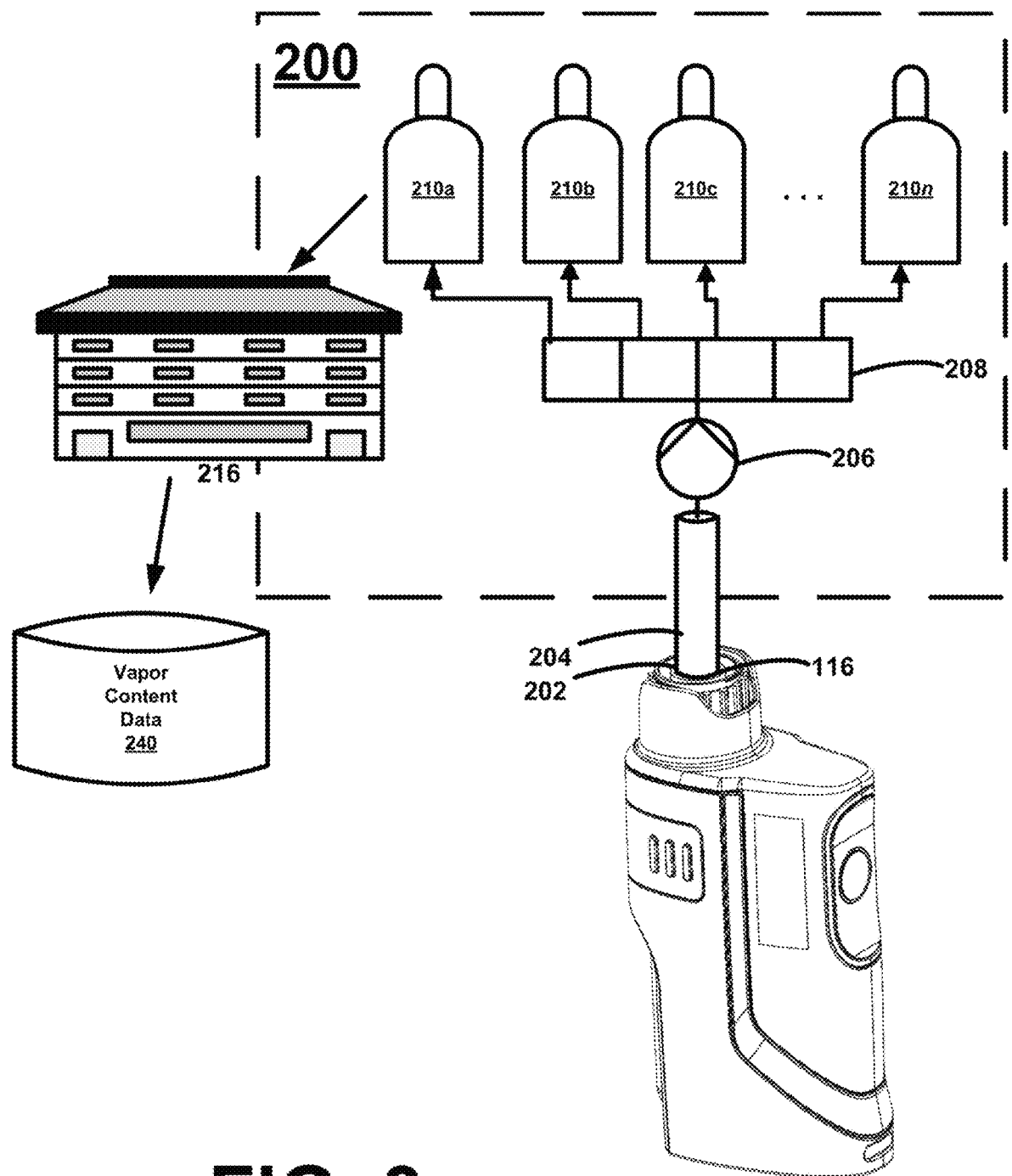
FIG. 3 is a schematic diagram of a vapor sample collection apparatus in accordance with the present disclosure.

FIG. 3 is a schematic diagram of a vapor sample collection apparatus 200 in accordance with the present disclosure. The vapor sample collection apparatus 200 includes a connection port 202 adapted to connect a first end of a tube 204 to an exhaust port 116 of a vaporizer device 100. Exhaust port 116 may be accessed by removing mouthpiece 114 so that connection port 202 can be connected thereto. Exhaust port 116 preferably has a similar fit to mouthpiece 114 that is sufficiently snug so that there is minimal loss of vapor at the connection port 202 to the outside world. A vacuum pump 206 may be connected to a second end of the tube 204, and a manifold 208 may be connected to the vacuum pump 206. Vapor containment vessels 210a-210n may be used for collecting vapor samples 212a-212n, where n is the number of vapor samples collected 216.

The vacuum pump 206 may be configured to draw a predetermined pressure on the tube 204 and may be metered to draw off the vaporized active compounds of a material for collection from vaporizer device 100. Vacuum pump 204 may be connected to a controller 214 to control the filling of vapor into collection vessels 210a-210n (where n is the number of vessels). Controller 214 controls vapor collection parameters such as vacuum pressure, flow rate and time of capture, and may also control manifold 208 to selectively allow capture in a single or multiple vapor containment vessels 210a-210n.

Vapor contained in vessels 210a-210n may be collected and analyzed by a laboratory 216. Analysis by a laboratory 216 may be performed using mass spectrometry or other laboratory techniques for quantifying and thus provide detailed information of the composition of contents of the captured vapor in vapor content data 240.

Figure 4:
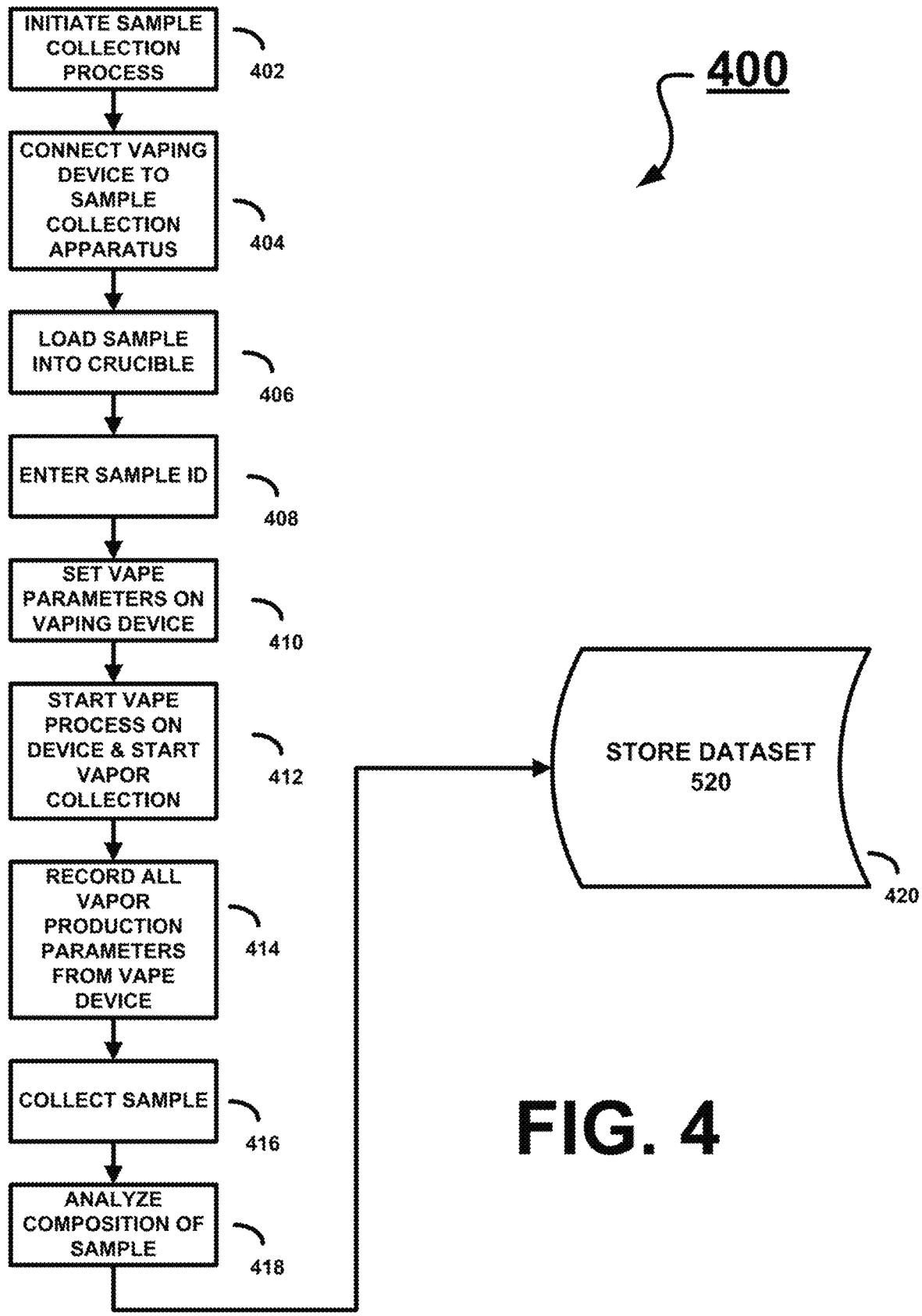
FIG. 4 is a flow diagram of an example process for capturing and quantification of vapor content according to the preset disclosure.

FIG. 4 is a flow diagram of an example process for capturing and quantification of vapor content 400 according to the present disclosure. Some steps shown in FIG. 4 may be performed by any suitable computer-executable code and/or computing system, including Vapor Profile Management System 500 in FIG. 5. Some of the steps shown in FIG. 4 may represent an algorithm whose structure includes and/or can be is represented by multiple sub-steps, examples of which will be provided in greater detail below.

The process 400 begins with initiation of a sample collection at step 402. Next, vaporizer device 100 is connected to sample collection apparatus 200 in step 404. Sample material containing an active ingredient is loaded into receptacle 126 on vaporizer device 100 at step 406. Next, a sample identifier is entered or captured that is associated with the sample material (e.g., QR code, barcode, serial number, etc.), at step 408. The process continues by setting the vaporizer parameters on the vaporizer device 100, at step 410. In sequence, the vaporizer process on device 100 is started and vapor is collected using sample collection apparatus 200, at step 412. Various vaporizer operating parameters and data from sensors 150 from vaporizer device 100 concerning the vapor production are recorded at step 414. The sample from vaporizer device 100 is drawn using the vapor sample collection apparatus 200 and stored in a vapor containment vessel(s) 210a-210n, to be analyzed by laboratory in step 416. A laboratory analyzes composition of the sample from vaporizer device 100 in step 418. Various vapor production data 190 from vaporizer device 100, sample collection apparatus 200 and various vapor content data 240 from the laboratory analysis may be transmitted over communications network 170 and stored in a dataset 600 in vaporizer profile management system 500, at step 420.

Determining the amounts of active ingredients extracted through the vaporizing process and present in the vapor in the most accurate way possible and informing the user and/or device of these amounts allows the device to deliver specified and tightly controlled quantity of active ingredients. Such is highly desirable to deliver accurate doses to users of vaporizer device 100.

Figure 5A:
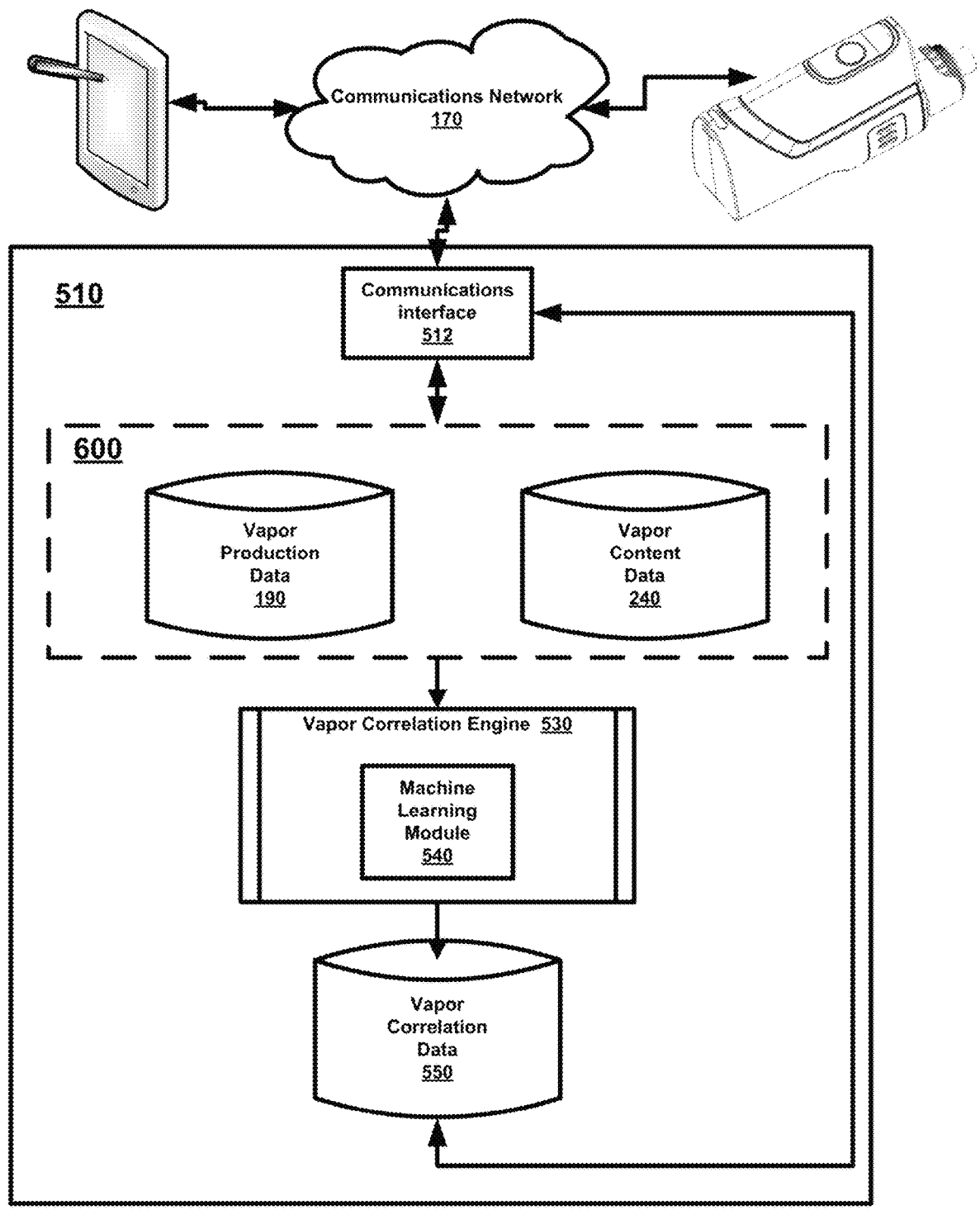
FIG. 5A is a schematic block diagram of a vaporizer profile management system in accordance with the present disclosure.

FIG. 5A is a schematic block diagram of a vaporizer profile management system ("VPMS") 500 in accordance with the present disclosure. VPMS 500 may include a computing platform 510 with a communications interface 512 to receive vapor production data 190 from vaporizer device 100, and to receive vapor content data 240 from a laboratory. Communications interface 512 may also have provision for receiving data imports from data storage means such as DVD, Blu-ray disks, flash memory, hard drives or any other physical data storage device.

Vapor data repository 520 stores vapor production data 190 and vapor content data 240 in a dataset 600.

Figure 5B:
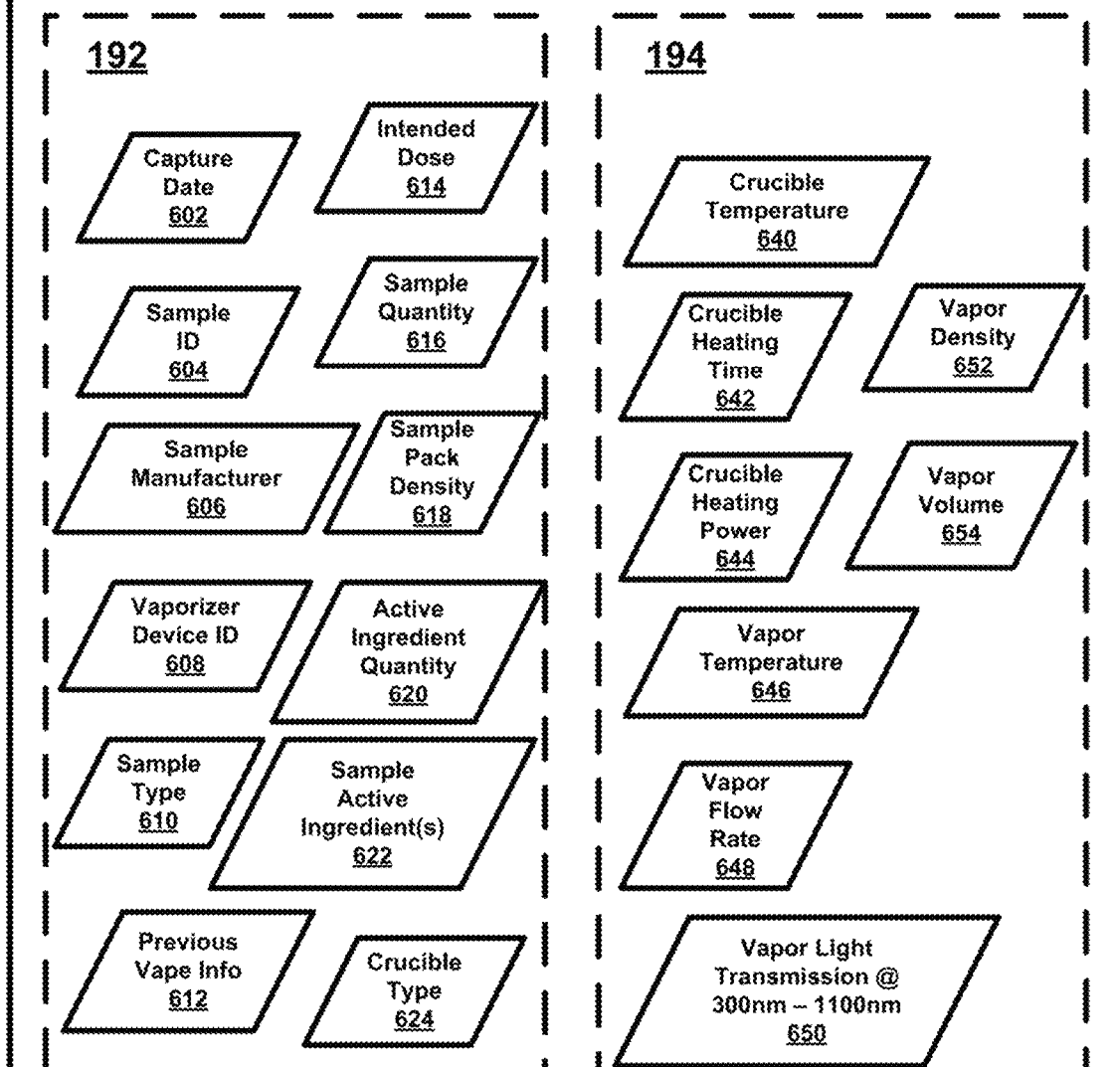
FIG. 5B is a schematic block diagram of a vapor production data dataset in accordance with the present disclosure.

FIG. 5B is a schematic block diagram of an example vapor production data dataset 190. Examples of vapor production data 190 may be data that is entered or captured by vaporizer device 100 (and/or connected mobile device application 182), as shown in data group 192. Examples of such data include capture date 602, sample identifier 604, sample manufacturer 606, vapor device ID 608, sample type 610, previous vape info 612, intended dose 614, sample quantity 616, sample pack density 618, active ingredient quantity 620, sample active ingredients 622, and Crucible type 624.

Data group 194 includes information that is captured by sensors during the production of vapor and may include Crucible temperature 640, Crucible heating time 642, Crucible heating power 644, vapor temperature 646, vapor flow rate 648, vapor light transmission 650, vapor density 652, vapor volume 654.

Figure 5C:
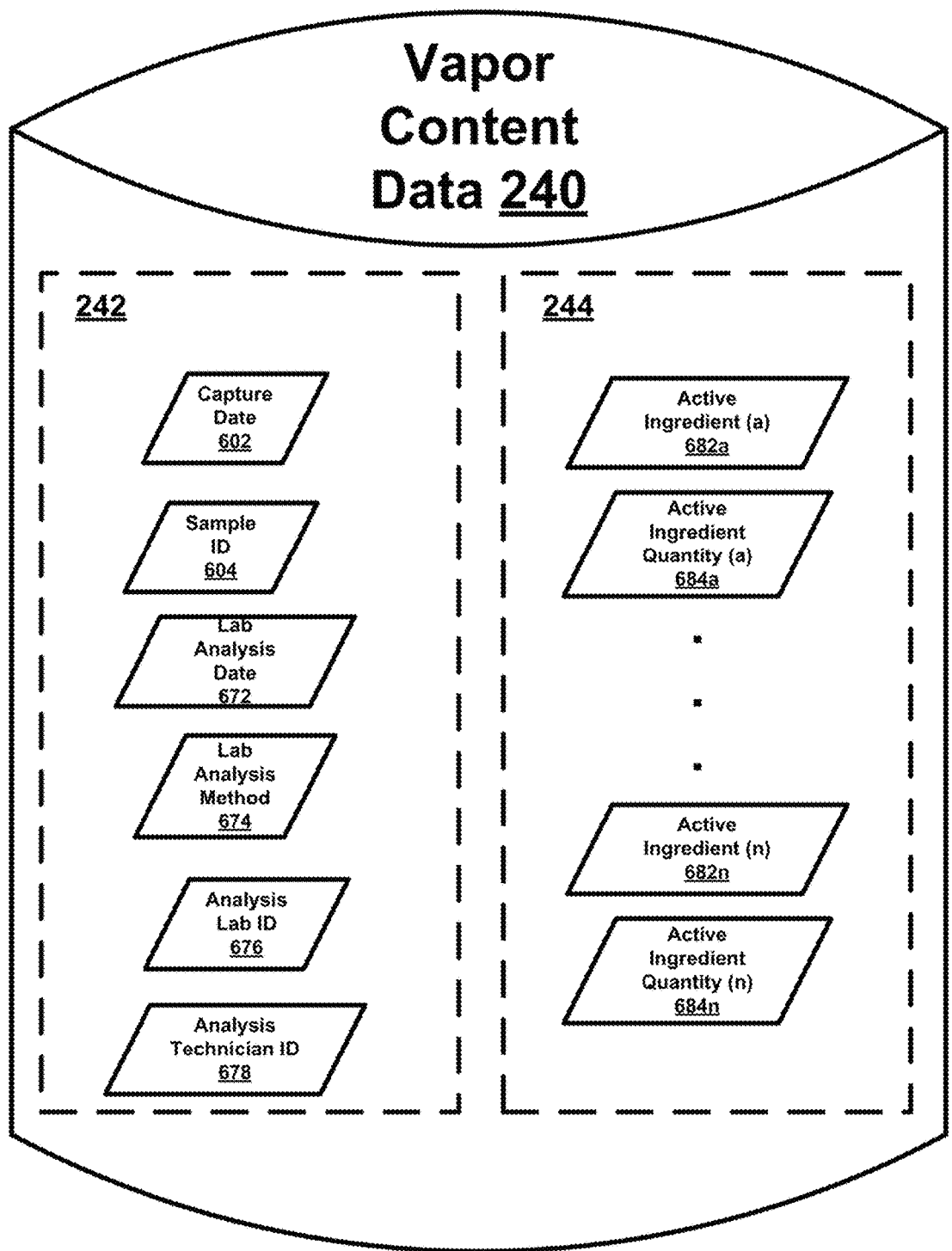
FIG. 5C is a schematic block diagram of a vapor content data dataset in accordance with the present disclosure.

FIG. 5C is a schematic block diagram of an example vapor content data dataset 240, which contains data that is received from a laboratory that analyzes the collected vapor sample. Data 242 includes parameters associated with the sample identification and other related metadata, while data group 244 includes data from the laboratory analysis. Data set 242 may include capture date 602, sample identifier 604, laboratory analysis date 672, laboratory analysis method 674, analysis lab ID 676, analysis technician ID 678. In general, it may be seen that these date fields may be helpful for an audit trail. Data set 244 may include measurement data of the sample(s) and will provide identified active ingredients and quantities for active ingredients a through n, where n is the number of active ingredients.

Referring back to FIG. 5A, vapor correlation engine 530 analyzes the dataset 600 and correlates vapor content data 240 and actual measured active ingredients measured in samples with vapor production data 190. Such correlation may be performed with machine learning module 540, which may use predictive analysis techniques, using vapor content data 240 and vapor production data 190 as input training data. Vapor correlation data 550 is generated, providing temperature-dependent extraction curves for each specific compound in a type of consumable material, associated with a sample identifier, along with production variables specific to use of vaporizer device 100 as measured by sensors 150 or input into vapor production data 190, such as draw speed, pack density of material, ambient temperature, and so on.

As used here, vapor correlation data 550 provides information that correlates dosage for active ingredient(s) in a particular material with operating parameters (e.g., heating element temperature and duration) for a vaporizer device. As more vapor correlation data 550 generated from the collected vapor production data 190 and vapor content data 240 is collected and analyzed as training data by machine learning module 540, this provides more accuracy in determining the temperature-dependent extraction curves described above. With increased collection and analysis of data, the curves become more accurate and can be represented in higher resolution, for example, by polynomial equations created from curve fitting the data to polynomial functions. The polynomial functions will be representative of extraction and dosing predictions across variables considered in the available data and will be able to correlate the vapor being produced to the specific compounds extracted from the consumable across relevant variables. Machine learning module 540 may use pattern recognition, extrapolation techniques, and probability predictions to match desired dose parameters for extracted chemical compounds with production parameters to be used on vaporizer device 100 to deliver such desired dose. A data set of vapor correlation data 550 is created, providing a database that may be queried for vaporizer production parameters to be used for a desired dose.

The data set of vapor correlation data 550 may be stored in the cloud and queried over communications network 170 on an as-needed basis or it may be downloaded and stored in a vaporizer profile on the vaporizer device 100 or mobile device application 182. The data set of vapor correlation data 550 (in whole or in part) may be updated and transmitted to device 100 or mobile application 182 in periodic or ad-hoc updates. Such updates may be for requested materials with active ingredient(s), or may provide a library of materials with active ingredient(s). A user of vaporizer device 100 may subscribe to a service that provides such vapor correlation data 550 updates, or may receive the relevant vapor correlation data 550 download upon entering or scanning a code on the packaging of material with active ingredient.

Figure 6:
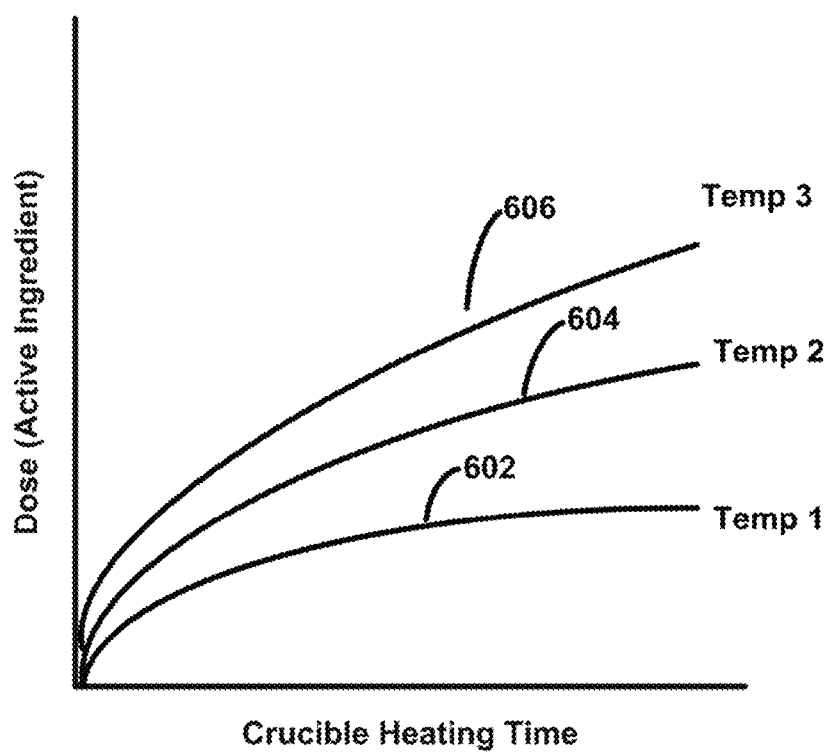
FIG. 6 is an exemplary graph showing measured amount of active ingredient(s) extracted in a vaporizer device 100 against crucible heating time for various different temperature profiles in accordance with the present disclosure.

FIG. 6 is an exemplary graph showing measured amount of active ingredient(s) extracted in a vaporizer device 100 against crucible heating time for various different temperature profiles. Such vapor content data 240 may be captured using the apparatus and capture method in the present disclosure, with the measured amount of active ingredient being analyzed by a laboratory. Other graphs may be plotted that showed the measured amount of active ingredient against other parameters, and the graph here is merely an example. Various different temperature profiles for different temperatures in the crucible may be plotted against time that the crucible is heated. As may be seen, the warmer the temperature, the more active ingredient of a particular type that may be released. However over time, the active ingredient is drawn out of the crucible and there is less concentration after a given time so the active ingredient yield curve flattens over time. Also plotted against crucible heating time and crucible heating temperature and captured in the dataset are the vapor production data 190. Vapor correlation data 550 may be determined using machine learning module 540 analyzing the correlation between training data that includes the measured amount of active ingredient(s) captured (from the vapor content data 240) and the vapor production data 190.

Figure 7:
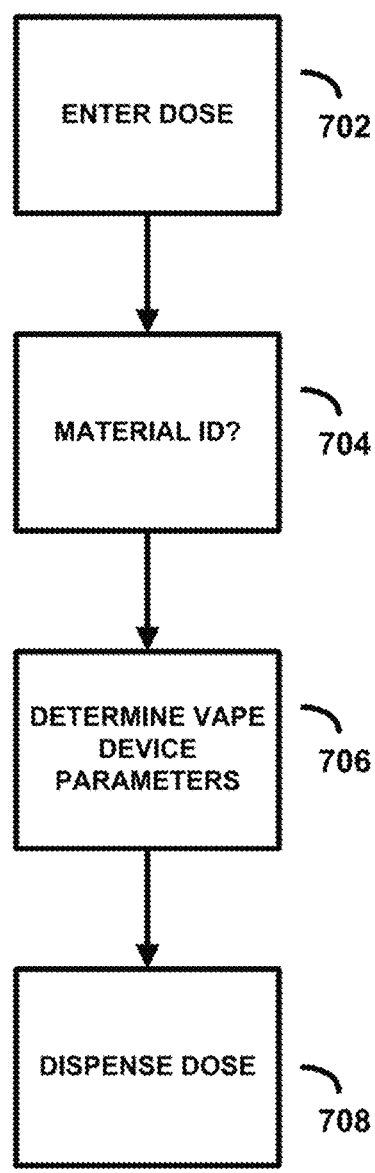
FIG. 7 is a flow diagram of a process for using a vaporizer profile management system to provide a selected dose of active ingredient in a vaporizer device in accordance with the present disclosure.

It should be noted that different active ingredients may have different optimum vaporizer extraction temperature/time combinations. Further, a partially-used or an aged sample of material may have a different extraction profile than a fresh sample. Vapor correlation data 550 may consider such different variables such as sample age and previous extraction cycles to determine optimum extraction parameters for vaporizer device 100. FIG. 7 is a flow diagram of a process for using a vaporizer device 100 with a vaporizer profile management system ("VPMS") 500, in accordance with the present disclosure. In step 702, dose information is entered into vaporizer device 100. This may be entered via a user interface on the device, or via application 182 running on mobile device 180, or through another connected interface device such as an internet browser interface, or a voice-controlled internet device running a compatible application e.g., Amazon Alexa, Google Hub, Apple Siri, etcetera. In step 704, the material is identified, and the material identifier is entered into vaporizer device 100. Again, this may be entered via any of the user interfaces or via camera recognition, barcode, QR code, or any other machine-identifiable code. In step 706, the vaporizer device parameters are determined to satisfy the dose request for the material. This may be a look up in memory on vaporizing device 100 itself, a look up stored on the app 182, or a look up stored in the cloud (e.g., a request to VPMS 300). In each case, the information is returned back to vaporizer device 100 to configure it to satisfy the dose request for the specified material. Next, the dose is dispensed in step 708 using the vaporizer production parameters selected to deliver the requested dose.

Various embodiments disclosed herein are to be taken in the illustrative and explanatory sense, and should in no way be construed as limiting of the present invention as defined in the appended claims. It is to be understood that individual features shown or described for one embodiment may be combined with individual features shown or described for another embodiment.

All numerical terms, such as, but not limited to, "first", "second", "third", or any other ordinary and/or numerical terms, should also be taken only as identifiers, to assist the reader's understanding of the various embodiments, variations, components, and/or modifications of the present disclosure, and are not intended to create any limitations, particularly as to the order, or preference, of any embodiment, variation, component and/or modification relative to, or over, another embodiment, variation, component and/or modification.

What is claimed is:

1. A vapor sample collection apparatus comprising:
   a connection port adapted to detachably connect a first end of a tube to an exhaust port of a vaporizer device;
   a vacuum pump connected to a second end of the tube;
   a manifold connected to the vacuum pump; and
   a vapor containment vessel for collecting a vapor sample, wherein the vacuum pump is configured to draw a predetermined pressure on the tube to provide the vapor sample from the vaporizer device to the vapor containment vessel via the exhaust port.

2. The vapor sample collection apparatus of claim 1, wherein the vaporizer device comprises:
   a receptacle for holding material having an active ingredient;
   a heating element for one of heating the receptacle or heating air as it flows to the receptacle;
   a vaporizer controller configured to receive vapor production information from sensors inside the vaporizer device, wherein the vaporizer controller is further configured to generate vapor production data comprising a sample identifier associated with the material and at least one of:
   crucible temperature, vapor temperature, vapor flow rate, vapor pressure, vapor flow duration, vapor density, heating duration, material pack density, pressure differential, material age, and heating power; and
   an electronic memory configured to store the vapor production data.

3. The vapor sample collection apparatus of claim 1, wherein the vaporizer device is configured to generate vapor production data.

4. The vapor sample collection apparatus of claim 1, wherein the exhaust port is accessed by removing a mouthpiece of the vaporizer device.

5. The vapor sample collection apparatus of claim 1, wherein the vacuum pump is configured to draw off a metered amount of material collected from the vaporizer device.

6. The vapor sample collection apparatus of claim 1, further comprising a controller connected to the vacuum pump, wherein the controller is configured to control the collection of the vapor sample into the vapor containment vessel.

7. The vapor sample collection apparatus of claim 6, wherein the vapor containment vessel comprises a plurality of collection vessels.

8. The vapor sample collection apparatus of claim 6, wherein the controller is configured to control vapor collection parameters comprising vacuum pressure, flow rate and time of capture.

9. The vapor sample collection apparatus of claim 6, wherein the controller is configured to control the manifold to selectively allow capture into a single vapor containment vessel or multiple vapor containment vessels.

10. The vapor sample collection apparatus of claim 1, wherein the manifold is coupled to a plurality of collection vessels, and the vacuum pump is configured to provide vapor generated by the vaporizer device to the plurality of collection vessels.

11. A method of vapor sample collection comprising:
    connecting a detachable connection port to an exhaust port of a vaporizer device, the detachable connection port being attached to a first end of a tube;
    activating the vaporizer device to vaporize a sample containing an active ingredient;
    drawing a predetermined pressure on a second end of the tube using a vacuum pump to provide a vapor sample from the vaporizer device to a vapor sample collection apparatus via the exhaust port; and
    collecting the vapor sample from the vaporizer device in a vapor containment vessel in the vapor sample collection apparatus.

12. The method of claim 11, further comprising drawing a metered amount of vapor collected from the vaporizer device.

13. The method of claim 11, further comprising controlling the collection of the vapor sample into the vapor containment vessel.

14. The method of claim 11, further comprising collecting the vapor sample into a plurality of collection vessels.

15. The method of claim 11, further comprising analyzing the vapor contained in the vapor containment vessel by a laboratory.

16. The method of claim 15, wherein the analysis of the vapor is performed using one of mass spectrometry and high performance liquid chromatography.

17. The method of claim 15, wherein the analysis provides detailed information of the composition of contents of the captured vapor.

18. The method of claim 11, wherein activating the vaporizer device further comprises generating vapor production information from sensors inside the vaporizer device.

19. The method of claim 11, further comprising generating vapor production data comprising a sample identifier associated with material from which the vapor sample was generated and at least one of:
    crucible temperature, vapor temperature, vapor flow rate, vapor pressure, vapor flow duration, vapor density, heating duration, material pack density, pressure differential, material age, and heating power.

20. The method of claim 19, further comprising providing the vapor production data to a remote cloud computing platform.

21. The method of claim 20, further comprising processing the vapor production data on a machine-learning module in communication with the remote cloud computing platform.

* * * * *